(12) United States Patent
Nielsen et al.

(10) Patent No.: US 7,097,837 B2
(45) Date of Patent: Aug. 29, 2006

(54) SYNTHETIC VACCINE AGENTS

(75) Inventors: Klaus Gregorius Nielsen, Horsholm (DK); Peter Koefoed, Horsholm (DK)

(73) Assignee: Pharmexa A/S, Horsholm (DK)

( * ) Notice: Subject to any disclaimer, the term of this patent is extended or adjusted under 35 U.S.C. 154(b) by 291 days.

(21) Appl. No.: 10/080,101

(22) Filed: Feb. 19, 2002

(65) Prior Publication Data

US 2002/0119162 A1 Aug. 29, 2002

Related U.S. Application Data

(63) Continuation-in-part of application No. PCT/DK01/00113, filed on Feb. 19, 2001, and a continuation-in-part of application No. 09/785,215, filed on Feb. 20, 2001.

(60) Provisional application No. 60/337,543, filed on Oct. 22, 2001.

(30) Foreign Application Priority Data

Aug. 20, 2001 (DK) ............................. 2001 01231

(51) Int. Cl.
A61K 39/00 (2006.01)
A61K 39/385 (2006.01)
A61K 38/00 (2006.01)
C07K 4/00 (2006.01)
C07K 17/00 (2006.01)

(52) U.S. Cl. .................. 424/144.1; 424/193.1; 424/184.1; 424/278.1; 514/2; 530/300; 530/350

(58) Field of Classification Search ............... 530/300, 530/350; 424/184.1, 178.1, 179.1, 183.1, 424/185.1, 193.1; 514/1, 2

See application file for complete search history.

(56) References Cited

U.S. PATENT DOCUMENTS

| 4,578,770 A | 3/1986 | Mitani |
|---|---|---|
| 4,596,792 A | 6/1986 | Vyas |
| 4,599,230 A | 7/1986 | Milich et al. |
| 4,599,231 A | 7/1986 | Milich et al. |
| 4,601,903 A | 7/1986 | Frasch |
| 4,608,251 A | 8/1986 | Mia |
| 5,200,339 A | 4/1993 | Abraham et al. |
| 5,223,482 A | 6/1993 | Schilling, Jr. et al. |
| 5,573,916 A * | 11/1996 | Cheronis et al. ............ 435/7.1 |
| 5,709,995 A * | 1/1998 | Chisari et al. .................. 435/5 |
| 5,780,036 A * | 7/1998 | Chisari .................... 424/189.1 |
| 5,874,469 A | 2/1999 | Maniar et al. |
| 6,713,450 B1 | 3/2004 | Frangione et al. |
| 6,787,523 B1 | 9/2004 | Schenk |
| 6,787,637 B1 | 9/2004 | Schenk |
| 2002/0077288 A1 | 6/2002 | Frangione et al. |
| 2004/0062802 A1 | 4/2004 | Hermelin et al. |
| 2004/0091945 A1 | 5/2004 | Fitzer-Atlas et al. |

FOREIGN PATENT DOCUMENTS

| WO | 93/15760 | 8/1993 |
|---|---|---|
| WO | WO 93/15760 | 8/1993 |
| WO | 93/23076 | 11/1993 |
| WO | WO 93/23076 | 11/1993 |
| WO | WO 94/03530 | 2/1994 |
| WO | WO 95/05849 | 3/1995 |
| WO | WO 95/07707 | 3/1995 |
| WO | 96/13513 | 5/1996 |
| WO | WO 98/23635 | 6/1998 |
| WO | WO 00/05316 | 2/2000 |
| WO | WO 00/20027 | 4/2000 |
| WO | WO 00/65058 | 11/2000 |

OTHER PUBLICATIONS

Skolnick & Fetrow (2000) "From genes to protein structure and function: novel applications of computational approaches in the genomic era." Trends in Biotech. 18(1): 34-39.*

Jobling & Holmes (1991) "Analysis of structure and function of the B Subunit of cholera toxin by the use of site-directed mutagenesis." Molecular Microbiology 5(7): 1755-67.*

Calvo-Calle et al. (Feb. 15, 1993) "Immunogenicity of Multiple Antigen Peptides Containing B and Non-Repeat T cell Epitopes of Circumsporozoite Protein of Plasmodium falciparum." The Journal of Immunology 150(4): 1403-1412.*

Calvo-Calle et al. (Feb. 15, 1993) "Immunogenicity of Multiple Antigen Peptides Containing B and Non-Repeat T cell Epitopes of the Circumsporozoite Protein of Plasmodium falciparum." The Journal of Immunology 150(4): 1403-1412.*

Sela et al. (Apr. 1992) "A Tale of Two Peptides, TyrTyrGluGlu and TyrGluTyrGlu, and their Diverse Immune Behavior." Behring Inst. Mitt. 91: 54-66.*

(Continued)

Primary Examiner—Christine J. Saoud
Assistant Examiner—Jon M. Lockard
(74) Attorney, Agent, or Firm—Sterne, Kessler, Goldstein & Fox P.L.L.C.

(57) ABSTRACT

The present invention provides for novel immungens that are comprised of an activated polyhydroxypolymer backbone to which is attached 2 separate antigenic determinants. The 1st antigenic determinant includes a B-cell or CTL epitope and the 2nd antigenic determinant includes a T-helper epitope. In preferred embodiments, the antigenic determinants are derived from different molecules and species. Exemplary immunogens of the invention are constituted of a linear tresyl-activated dextran backbone to which is coupled B-cell or CTL epitopes of an antigen and to which is also coupled universal T-helper epitopes. Also disclosed are immunogenic compositions comprising the immunogens, methods of immunization and a method for identification of suitable immunogens of the invention.

23 Claims, 1 Drawing Sheet

OTHER PUBLICATIONS

Goldsby et al. (2002) Kuby Immunology Chapter 1 "Overview of the Immune System" (pp. 3-25).*
Goldsby et al. (2002) Kuby Immunology Chapter 18 "Vaccines" (pp. 449-465).*
Gregorius and Theisen, "In Situ Deprotection: A method for Covalent Immobilization of Peptides with well-defined orientation for use in solid phase immunoassays such as enzyme-linked immunosorbent assay" (2001) Analytical Biochemistry 299:84-91.
Barr and Mitchell, "ISCOMs (immunostimulating complexes): The first decade " Immunology and Cell Biology (1996) 74: 8-25.
Gosselin et al. "Enhanced Antigen Presentation using Human Fc$\square$ Receptor (Monocyte/Macrophage)-specific immunogens" (1992) 149:3477-3481.
Nilsson and Mosbach (1987) "Supports for Enzyme Immobilization " Methods in Enzymology 135: 67.
Hemansson et al. "Immobilized affinity ligand techniques " (1992) 87.
Morein et al. "Immunostimulating Complexes, Clinical Potential Vaccine Development" Clin. Immunotherapy (1995) 3(6): 460-475.
Irving et al. "Random-peptide libraries and antigen-fragment libraries for epitope mapping and the development of vaccines and diagnostics" Current Opinion in Chemical Biology (2001) 5:314-324.
Nelson et al. "Monoclonal antibodies" Molecular Pathology, Accepted for publication Feb. 8, 2000.
Nussinov and Wolfson, Efficient Computational Algorithms for Docking and for generating and matching a library of functional epitopes II. Computer Vision-based techniques for the generation and utilization of functional epitopes. (1999) Combinatorial Chemistry and High Throuput Screening 2: 261-269.
De Groot et al. "From genome to vaccine: in silico predictions, ex vivo verification" Vaccine 19 (2001) 4385-4395.
Rammensee et al. "MHC ligands and peptide motifs: first listings" Immunogenetics (1995) 41: 178-228.
Schirle et al. "Identification of tumor-associated MHC class I ligands by a novel T cell-independent approach" Eur. J. immunol, (2000) 30: 2216-2225.
Southwood et al. "Several Common HLA-DR Types share largely overlapping peptide binding repertoires" The Journal of Immunology, 1998, 160: 3363-3373.
Singigaglia et al. "A malaria T-cell epitope recognized in association with most mouse and human MHC class II molecules" Nature vol. 336 Dec. 22-29 1988, 778-780.
Chicz et al. "Specificity and Promiscuity among naturally processed peptides bound to HLA-DR Alleles" (1993) J. Exp. Med. 178: 27-79.
Hammer et al. "Promiscuous and Allele-specific anchors in HLA-DR-Binding Peptides" (1993) Vell, vol. 197-203.
Falk et al. "Pool sequencing of natural HLA-DR, DQ, and DP ligands reveals detailed peptide motifs, constraints of processing and general rules" Immmunogenetics (1994) 39: 230-242.
Alexander et al. "Serum interleukin 5 concentrations in atopic and non-atopic patients with glucocorticoid-dependent chronic severe asthma" Thorax (1994) 49:1231-1233.
Dempsey et al. "C3d of complement as a molecular adjuvant: bridging innate and acquired immunity" (1996) Science 271: 348.
Lou and Kohler, "Enhanced molecular mimicry of CEA using photoaffinity crosslinked C3d peptide" Nature Biotechnology (1998) 16: 458-462.
Gregorius et al. "Hydrocoating: a new method for coupling biomolecules to solid phases" Journal of Immunological Methods (1995) 181:65-73.
Calvo-Calle, et al.; "Immunogenicity of Multiple Antigen Peptides Containing B and Non-Repeat T cell Epitose of the Circumsporozoite Protein of Plaemodium Falciparum"; The Journal of Immunology (1993); vol. 150(4); pp. 1403-1412.
Goldsby, et al.; "Overview of the Immune System"; Kuby Immunology (2002); Chapter 3; pp. 3-25.
Goldsby, et al.; "Vaccines"; Kuby Immunology(2002); chapter 18; pp. 449-465.
Lees, et al.; "Enhanced Immunogenicity of Protein-Dextran Conjugates: I. Rapid Stimulation of Enhanced Antibody responses to Poorly Immunogenic Molecules:"; Vaccine(1994); vol. 12(13); pp. 1160-1166.
Marguerite, M., et al; "Analysis of Antigenicity and Immunogenicity of five Different Chemically Defined Constructs of a Peptide"; Molecular Immunology(1992); vol. 29(6); pp. 793-800.
Otvos, et al.; "In Situ Stimulation of a T Helper cell Hybridoma with a Cellulose-bound peptide Antigen"; Journal of Immunological Methods(2000); vol. 233 (1-2); pp. 95-105.
Sela, et al.; "A tale of Two Peptides, TyrtyrGluGlu and TryGluTyrGlu, and their diverse Immune Behavior"; Behring Inst. Mitt. vol. 91; pp. 54-66.

* cited by examiner

PEPCOVAC SYNTHESIS

Fig. 1 peptide A
peptide B
tresyl activated dextran, TAD

Purification

SYNTHETIC VACCINE AGENTS

CROSS-REFERENCE TO RELATED APPLICATIONS

This application is a Continuation-in-Part application of International Application PCT/DK01/00113 filed Feb. 19, 2001, and is also a Continuation-in-Part application of U.S. application Ser. No. 09/785,215, filed Feb. 20, 2001. This application claims the benefit of U.S. Provisional Application No. 60/337,543, filed and Oct. 22, 2001, and claims priority to Danish Patent Application Number PA 2001 01231 filed Aug. 20, 2001 and to International Application Number PCT/DK02/00112, filed Feb. 19, 2002.

Each of the foregoing applications and patents and articles, and each document cited or referenced in each of the foregoing applications and patents and articles, including during the prosecution of each of the foregoing applications and patents ("application and article cited documents"), and any manufacturer's instructions or catalogues for any products cited or mentioned in each of the foregoing applications and patents and articles and in any of the application and article cited documents, are hereby incorporated herein by reference. Furthermore, all documents cited in this text, and all documents cited or referenced in documents cited in this text, and any manufacturer's instructions or catalogues for any products cited or mentioned in this text or in any document hereby incorporated into this text, are hereby incorporated herein by reference. Documents incorporated by reference into this text or any teachings therein may be used in the practice of this invention. Documents incorporated by reference into this text are not admitted to be prior art. Furthermore, authors or inventors on documents incorporated by reference into this text are not to be considered to be "another" or "others" as to the present inventive entity and vice versa, especially where one or more authors or inventors on documents incorporated by reference into this text are an inventor or inventors named in the present inventive entity.

FIELD OF THE INVENTION

The present invention provides for novel vaccine agents, which have a controllable distribution of different, well-defined peptides and which allows for detachment of these peptides from the agent by means of peptidase cleavage.

BACKGROUND OF THE INVENTION

Agents for immunizing or vaccinating animals include a large variety of different solutions to various problems involved in immunization.

When immunizing with small antigens or haptens, one problem is often the absence of peptide sequences in the immunogen that can trigger CD4+ cells to provide the necessary help for B-cell or CTLs to mount a sufficient immune response. This problem is especially important when the antigen is of self-origin.

The traditional approach has been to covalently couple (conjugate) the antigen of interest to a large immunogenic carrier protein. In recent years this technology has been refined by utilising immunogens comprised of short peptide antigens fused to relevant carrier proteins or even to known universal T-helper epitopes.

However, both of these prior art technologies suffer a number of drawbacks. If using the traditional carrier approach, it is difficult to characterise the resulting product and it is further a problem that the immune response induced will have a tendency to be directed towards the carrier moiety and not to towards the peptide antigen—this phenomenon is known as "carrier suppression".

Furthermore, when coupling a small peptide to a large carrier, it is normally not predictable whether or not the antigenic determinant(s) of the peptide will be accessible to the immune system, since the carrier moiety to some degree will shield the peptide.

Similar problems exist with fusion of carriers to peptides—this problem is to some extent avoided when using "carriers" that are constituted of short T-helper epitopes. Nevertheless, this may also give rise to problems. Due to the small size of both the peptide and the T-helper epitope, it is not in any way a certain thing that the ratio between T-helper epitopes and antigenic determinant is optimal in order to trigger the most effective immune response.

In conclusion, there is a definite need to device novel strategies for preparing vaccine based on small antigenic peptides or small haptens.

OBJECT OF THE INVENTION

It is an object of the present invention to provide for novel immunogenic agents that utilise an inert carrier as a multivalent coupling agent to which one can couple both an antigen of interest but also a controlled amount of T-helper epitopes and/or other immunologically suitable moieties. It is a further object of the invention to provide for compositions including such immunogenic agents as well as to provide for novel methods of immunization.

SUMMARY OF THE INVENTION

One known way of achieving coupling of peptides to an immunologically inert carrier is to activate a suitable polyhydroxypolymer with tresyl (trifluoroethyl-ulphonyl) groups or other suitable activation groups such as maleimido, p-Nitrophenyl cloroformate (for activation of OH groups and formation of a peptide bond between peptide and polyhydroxypolymer), and tosyl (p-toluenesulfonyl). It is e.g. possible to prepare activated polysaccharides as described in WO 00/05316 and U.S. Pat. No. 5,874,469 (both incorporated by reference herein) and couple these to peptides that have been prepared by means of conventional solid or liquid phase peptide synthesis techniques. The resulting product consists of a polyhydroxypolymer backbone (e.g. a dextran backbone) that has, attached thereto by their N-termini or by other available nitrogen moieties, peptides of choice.

This known way of coupling peptides (or other suitable antigenic determinants) to e.g. tresylated water-soluble dextran has to the best of the present inventors' knowledge previously merely been contemplated for dianogstic uses. However, the present inventors have now surprisingly discovered that such peptide-polyhydroxypolymer conjugates are very suitable as agents for immunisation. This has been demonstrated in a series of experiments where a mixture of a C-terminal peptide (the 8 C-terminal amino acids) from the Borrelia antigen OspC and a known $T_H$ epitope peptide was coupled to a tresyl-activated dextran and used as an immunization agent in mice.

However, this principle or coupling a peptide antigen to a polyhydroxypolymer is in the opinion of the present inventors a generally applicable, novel and inventive approach:

Molecules can be obtained that comprise a T helper epitope and molecules representing or including B-cell epitopes linked covalently to a non-immunogenic polymer molecule acting as a vehicle, e.g. a multivalent activated poly-hydroxypolymer—this type of molecule functions as a vaccine molecule that only contains the immunologically relevant parts of antigens. Promiscuous or so-called universal T-helper epitopes can be used if e.g. the target for the vaccine is a hapten (such as a self-antigen) or an antigen that otherwise could be rendered more immunogenic by adding further $T_H$ epitopes. Furthermore, elements that enhance the immunological response could be also co-coupled to the vehicle and thereby act as an adjuvant. Such elements could be mannose, tuftsin, muramyl dipeptide, CpG motifs etc, cf. below. In that case, subsequent adjuvant formulation of the vaccine product might be unnecessary and the product could be administered in pure water or saline.

By coupling cytotoxic T cell (CTL) epitopes together with the T-helper epitopes it will also be possible to generate CTL's specific for the antigen from which the CTL epitope was derived. Elements that promote uptake of the product to the cytosol, such as mannose, of the APC, e.g. a macrophage, could also be co-coupled to the vehicle together with the CTL- and the T helper epitope and enhance the CTL response.

Hence, in its most broad and general scope, the present invention provides for a novel immunogen which comprises a) at least one first antigenic determinant that includes at least one B-cell epitope and/or at least one CTL epitope, and b) at least one second antigenic determinant that includes a T helper cell epitope ($T_H$ epitope), wherein each of the at least one first and second antigenic determinants are coupled to a pharmaceutically acceptable activated polyhydroxypolymer carrier.

Another aspect of the invention relates to an immunogenic composition comprising the immunogen of the invention.

A third aspect of the invention relates to a method of immunizing/vaccinating an animal against an antigen of choice by administering the immunogen or the immunogenic composition of the invention, where the immunogen and the antigen of choice shares the same at least one first antigenic determinant.

A fourth aspect of the invention relates to a method for preparing and selecting useful immunogens of the invention.

It should be noted that the present disclosure focuses on the use of antigenic peptide determinants—in fact it is necessary that the $2^{nd}$ antigenic determinant is, or at least contains, an amino acid sequence that constitutes an MHC Class II binding peptide (a $T_H$ epitope). However, if the $1^{st}$ determinant includes B-cell epitopes, it need not necessarily be a peptide—it will be understood by the skilled reader that all disclosures relating to the $1^{st}$ antigenic determinant may relate to other B-cell epitope-containing molecular entities, unless the present disclosure specifically discusses characteristics of $1^{st}$ peptide determinants that would not be applicable to other antigenic determinants (for instance in the event the $1^{st}$ determinant is a CTL epitope).

LEGEND TO THE FIGURE

FIG. 1: Schematic drawing of the synthesis of immunogens of the invention, exemplified by peptide-coupling to TAD. A mixture of peptides A and B is brought in contact (essentially as described in Example 2) with a tresyl-activated, water-soluble dextran. Peptides A and B react with the activation groups on the TAD, and after purification the immunogen is provided.

DETAILED DISCLOSURE OF THE INVENTION

Definitions

In the following, a number of terms used in the present specification and claims will be defined and explained in detail in order to clarify the metes and bounds of the invention.

The terms "T-lymphocyte" and "T-cell" will be used interchangeably for lymphocytes of thymic origin that are responsible for various cell mediated immune responses as well as for helper activity in antigen specific immune responses. Likewise, the terms "B-lymphocyte" and "B-cell" will be used interchangeably for antibody-producing lymphocytes. The terms "cytotoxic T-cell", "cytotoxic T lymphocyte" and the term "CTL" are also used interchangeably for lymphocytes that induce cell killing in response to recognition of peptide sequences bound to MHC Class I molecules on the surface of the cells.

"An immunogen" is herein meant to designate a single molecule that includes one or more antigenic determinants of an antigen of interest and one or more $T_H$ epitopes that are recognized by the animal to be immunized.

"Antigenic determinant" is herein designating a molecule or a part of a molecule that is specifically recognised by certain clones of lymphocytes. An antigenic determinant may e.g. be a B-cell epitope and thus recognized by B-cells and their corresponding antibodies. A B-cell epitope is characterized by its 3D shape and in essence any part of a molecule that can fit into the antigen binding site of an antibody may constitute an antigenic determinant of that molecule. Other antigenic determinants are CTL and $T_H$ epitopes—these are always peptides or contains peptides and they are characterized by their linear structure.

The term "peptide" is in the present context intended to mean both short peptides of from 2 to 10 amino acid residues, oligopeptides of from 11 to 100 amino acid residues, and polypeptides of more than 100 amino acid residues. Furthermore, the term is also intended to include proteins, i.e. functional biomolecules comprising at least one polypeptide. The peptide may be glycosylated and/or lipidated and/or comprise prosthetic groups.

The term "subsequence" means any consecutive stretch of at least 3 amino acids or, when relevant, of at least 3 nucleotides, derived directly from a naturally occurring amino acid sequence or nucleic acid sequence, respectively.

The term "animal" is in the present context in general intended to denote an animal species (preferably mammalian), such as Homo sapiens, *Canis domesticus*, etc. and not just one single animal. However, the term also denotes a population of such an animal species, since it is important that the individuals immunized according to the invention all harbour substantially the same antigen allowing for immunization of the animals with the same immunogen(s). If, for instance, genetic variants of the antigen exists in different human populations it may be necessary to use different immunogens in these different populations in order to be able to break the tolerance towards the antigen in each population. It will be clear to the skilled person that an animal in the present context is a living being which has an immune system. It is preferred that the animal is a vertebrate, such as a mammal.

The expression "effecting presentation . . . to the immune system" is intended to denote that the animal's immune system is subjected to an immunogenic challenge in a controlled manner. As will appear from the disclosure below, such challenge of the immune system can be by vaccination with peptide-containing immunogens of the invention. The important result to achieve is that immune competent cells in the animal are confronted with the antigen in an immunologically effective manner, whereas the precise mode of achieving this result is of less importance to the inventive idea underlying the present invention.

The term "immunogenically effective amount" has its usual meaning in the art, i.e. an amount of an immunogen which is capable of inducing an immune response which significantly engages agents (e.g. pathogenic agents) which share immunological features with the immunogen.

When discussing "autotolerance towards an autologous antigen" it is understood that since the relevant antigen is a self-molecule in the population to be vaccinated, normal individuals in the population do not mount an immune response against it; it cannot be excluded, though, that occasional individuals in an animal population might be able to produce antibodies against the native antigen, e.g. as part of an autoimmune disorder. At any rate, an animal species will normally only be autotolerant towards its own antigen, but it cannot be excluded that analogues derived from other animal species or from a population having a different phenotype would also be tolerated by said animal. Furthermore, antigens that lack size or (normally more relevant) $T_H$ epitopes are also tolerated by the immune system and these will behave in much the same way as a true self-antigen.

A "foreign T-cell epitope" (or: "foreign T-lymphocyte epitope") is a peptide which is able to bind to an MHC molecule and which stimulates T-cells in an animal species. Preferred foreign T-cell epitopes in the invention are "promiscuous" (or "universal" or "broad-range") epitopes, i.e. epitopes which bind to a substantial fraction of a particular class of MHC molecules in an animal species or population. Only a very limited number of such promiscuous T-cell epitopes are known, and they will be discussed in detail below. It should be noted that in order for the immunogens which are used according to the present invention to be effective in as large a fraction of an animal population as possible, it may be necessary to 1) insert several foreign T-cell epitopes in the same immunogen or 2) prepare several immunogens wherein each analogue has a different promiscuous epitope inserted. It should be noted also that the concept of foreign T-cell epitopes also encompasses use of cryptic T-cell epitopes, i.e. epitopes which are derived from a non-immunogenic protein and which only exerts immunogenic behaviour when existing in isolated form without being part of the non-protein in question.

A "foreign T helper lymphocyte epitope" (a foreign $T_H$ epitope) is a foreign T cell epitope which binds an MHC Class II molecule and can be presented on the surface of an antigen presenting cell (APC) bound to the MHC Class II molecule.

An "MHC Class II binding amino acid sequence that is heterologous to an antigen" is therefore an MHC Class II binding peptide that does not exist in the multimeric protein in question. Such a peptide will, if it is also truly foreign to the animal species harbouring the multimeric protein, be a foreign $T_H$ epitope.

A "functional part" of a (bio)molecule is in the present context intended to mean the part of the molecule which is responsible for at least one of the biochemical or physiological effects exerted by the molecule. It is well-known in the art that many enzymes and other effector molecules have an active site which is responsible for the effects exerted by the molecule in question. Other parts of the molecule may serve a stabilizing or solubility enhancing purpose and can therefore be left out if these purposes are not of relevance in the context of a certain embodiment of the present invention.

The term "adjuvant" has its usual meaning in the art of vaccine technology, i.e. a substance or a composition of matter which is 1) not in itself capable of mounting a specific immune response against the immunogen of the vaccine, but which is 2) nevertheless capable of enhancing the immune response against the immunogen. Or, in other words, vaccination with the adjuvant alone does not provide an immune response against the immunogen, vaccination with the immunogen may or may not give rise to an immune response against the immunogen, but the combination of vaccination with immunogen and adjuvant induces an immune response against the immunogen which is stronger than that induced by the immunogen alone.

"Targeting" of a molecule is in the present context intended to denote the situation where a molecule upon introduction in the animal will appear preferentially in certain tissue(s) or will be preferentially associated with certain cells or cell types. The effect can be accomplished in a number of ways including formulation of the immunogen in a composition facilitating targeting or by introduction in the immunogen of groups which facilitates targeting. These issues will be discussed in detail below.

"Stimulation of the immune system" means that a substance or composition of matter exhibits a general, non-specific immunostimulatory effect. A number of adjuvants and putative adjuvants (such as certain cytokines) share the ability to stimulate the immune system. The result of using an immunostimulating agent is an increased "alertness" of the immune system meaning that simultaneous or subsequent immunization with an immunogen induces a significantly more effective immune response compared to isolated use of the immunogen.

The term "polyhydroxypolymer carrier" is intended to denote the part of the immunogen that carries the amino acid sequences. As a general rule, the polyhydroxypolymer carrier has its outer limits where amino acid sequences can be cleaved of by a peptidase, e.g. in an antigen presenting cell that is processing the immunogen. Hence, the polyhydroxypolymer carrier can be the polyhydroxypolymer with an activation group, where the bond between the activation group and the amino acid sequence is cleavable by a peptidase in an APC, or the polyhydroxypolymer carrier can be a polyhydroxypolymer with activation group and e.g. a linker such as a single L-amino acid or a number of D-amino acids, where the last part of the linker can bond to the amino acid sequences and be cleaved by a peptidase in an APC.

The term "polysaccharide" is intended to be used with its normal meaning, i.e. "a combination of nine or more monosaccharides, linked together by glycosidic bonds", cf. Hawley's Condensed Chemical Dictionary, 11$^{th}$ ed., Sax and Lewis, eds., Van Nostrand Reinhold co., New York, 1987. Examples of such polysaccharides are dextran (e.g. Dextran 40, Dextran 70, Dextran 75), agarose, cellulose and starch.

1$^{st}$ and 2$^{nd}$ Antigenic Determinants

The rationale behind the present invention is that the provision of synthetic immunogens (especially peptide-containing immunogens) provides a greater deal of control over the composition of the end-product. In contrast, when using recombinantly produced polypeptide immunogens, purification and characterization is always a major task. Hence, in cases where specific antigenic determinants (epitopes) can be identified that are suitable as the main constituent in an immunogen, the present invention provides for a convenient way of preparing the immunogens in a cost-effective manner.

For most antigens, epitopes (both B-cell epitopes and CTL epitopes) are already known and published in the scientific literature—in practice a known protein may be "scanned" for epitopes by preparing overlapping truncates thereof that are reacted with monoclonal antibodies raised against the protein. The fragments that react with the antibody constitute local epitopes. Other suitable technologies include those described in Irving M B et al., Curr Opin Chem Biol 2001 5(3):314–24, Parker C E and Tomer K B, Methods Mol Biol 2000;146:185–201, and Nelson P N et al., Mol Pathol 2000; 53(3):111–7. Methods for prediction of epitopes are described in Nussinov R and Wolfson H J, Comb Chem High Throughput Screen 1999;2(5):261–9 Furthermore, methods of predicting and mapping the presence of epitopes (especially in protein antigens) via computer algorithms are also well-known in the art. For instance, CTL epitopes may be predicted via the methods described in Rothbard et al. EMBO J. 7:93–100 (1988) and in de Groot M S et al., Vaccine 2001;19(31):4385–95 or otherwise identified via the technologies described in Rammensee H-G. et al. (1995), Immunogenetics 41: 178–228, Schirle M et al. Eur J Immunol 2000;30(18):2216–2225.

Hence, it is especially preferred that either or both of the at least one first and second antigenic determinants of the immunogen are peptides, i.e. that they are constituted by amino acid sequences—since the $1^{st}$ and $2^{nd}$ amino acid sequences are normally attached separately to the activated polyhydroxypolymer carrier, their respective lengths can be kept at a minimum, thus facilitating the synthesis steps for each peptide species. The length of such amino sequences are contemplated to range from about 4 amino acids to about 100 (even though there is no upper limit), but preferably the upper limit will not exceed 80 amino acids, and it is preferred that the upper limit does not exceed 60 amino acids. Especially preferred lengths of peptidic antigenic determinants are thus in the range between about 4 to about 50 amino acids. Even lower upper limits are envisaged, such as at most 40, at most 30 and at most 25 amino acids. It is especially preferred that a peptidic antigenic determinant is constituted by an amino acid sequence of 4, 5, 6, 7, 8, 9, 10, 11, 12, 13, 14, 15, 16, 17, 18, 19, 20, 21, 22, 23, 24, or 25 amino acids. It is also contemplated to utilise e.g. recombinantly produced polypeptides as the molecule constituting the 1st antigenic determinant and using synthetic peptides as the $2^{nd}$ antigenic determinant. This would e.g. provide for conjugates where a full-length self-polypeptide is coupled to the carrier and the $T_H$ epitopes are coupled in other positions. It should thereby be possible to attach the necessary $T_H$ epitopes (perhaps several species) to the same molecular entity, without substantially interfering with the 3D structure of the self-polypeptide and thereby break tolerance.

In order to obtain processing and presentation of peptides of the immunogen by antigen presenting cells (APCs), the APCs must be able to cleave off the peptide antigenic determinant from the polyhydroxypolymer carrier. This is most conveniently achieved by having such a peptide antigenic determinant coupled to the carrier via a bond that can be cleaved by a peptidase, such as the peptidases that are active in the APCs' processing of peptide sequences. This can e.g. be achieved by having the determinants coupled to the carrier by means of a peptide bond or an amide bond. In preferred embodiments the antigenic determinant is bound to the carrier, where the antigenic determinant provides for the nitrogen atom of the amide or peptide bond—for peptidic antigenic determinants, this has the consequence that the peptide has a free carboxy terminus, an effect obtained when using a tresyl group as the activation group.

In many cases the $1^{st}$ and $2^{nd}$ antigenic determinants will be derived from different molecules, i.e. they are not found in the same molecule in nature. Further, it is normally also the case that they are not derived from the same species. And, even though it is preferred that the $1^{st}$ and $2^{nd}$ antigenic determinants are coupled independently to the activated polyhydroxypolymer it can be envisaged that they are e.g. fused to each other and coupled to the carrier at the terminus of the fusion product—this will be feasible when both antigenic determinants are relatively small (such as when the $1^{st}$ antigenic determinant is a CTL epitope and the $2^{nd}$ is a pure $T_H$ epitope).

The $2^{nd}$ antigenic determinant preferably includes an immunodominant $T_H$ epitope, that is, epitope which in the vaccinated individual gives rise to a significant immune response, but it is a well-known fact that a $T_H$ epitope which is immunodominant in one individual is not necessarily immunodominant in another individual of the same species, even though it may be capable of binding MHC Class II molecules in the latter individual. However, normally it will suffice to utilise a peptide that strongly binds to an MHC class II molecule.

With respect to the issues of particular considerations concerning immunodominance and MHC restriction of T helper epitopes, reference is made to e.g. WO 00/65058 and WO 00/20027 where thorough descriptions can be found.

The $T_H$ epitope being part of the $2^{nd}$ antigenic determinant is preferably a promiscuous $T_H$ epitope. There exist a number of naturally occurring promiscuous T-cell epitopes which are active in a large proportion of individuals of an animal species or an animal population and these are preferably introduced in the vaccine thereby reducing the need for a very large number of different modified $2^{nd}$ antigenic determinants in the same vaccine immunogen or in the same vaccine composition.

The promiscuous epitope can according to the invention be a naturally occurring human $T_H$ epitope such as epitopes from tetanus toxoid (e.g. the P2 and P30 epitopes, cf. SEQ ID NOs: 1 and 2, respectively), diphtheria toxoid, Influenza virus hemagluttinin (HA), and P. falciparum CS antigen.

Over the years a number of other promiscuous T-cell epitopes have been identified. Especially peptides capable of binding a large proportion of HLA-DR molecules encoded by the different HLA-DR alleles have been identified and these are all possible T-cell epitopes to be introduced in modified CEA used according to the present invention. Cf. also the epitopes discussed in the following references which are hereby all incorporated by reference herein: WO 98/23635 (Frazer IH et al., assigned to The University of Queensland); Southwood S et. al, 1998, J. Immunol. 160: 3363–3373; Sinigaglia F et al., 1988, Nature 336: 778–780; Rammensee H G et al., 1995, Immunogenetics 41: 4178–28; Chicz R M et al., 1993, J. Exp. Med 178: 27–47; Hammer J et al., 1993, Cell 74: 197–203; and Falk K et al., 1994, Immunogenetics 39: 230–242. The latter reference also deals with HLA-DQ and -DP ligands. All epitopes listed in these 5 references are relevant as candidate natural epitopes to be used in the present invention, as are epitopes which share common motifs with these.

Alternatively, the epitope can be any artificial T-cell epitope which is capable of binding a large proportion of haplotypes. In this context the pan DR epitope peptides ("PADRE") described in WO 95/07707 and in the corresponding paper Alexander J et al., 1994, Immunity 1:

751–761 (both disclosures are incorporated by reference herein) are interesting candidates for epitopes to be used according to the present invention. It should be noted that the most effective PADRE peptides disclosed in these papers carry D-amino acids in the C- and N-termini in order to improve stability when administered. However, the present invention primarily aims at incorporating the relevant epitopes as part of the immunogen which should then subsequently be broken down enzymatically inside the lysosomal compartment of APCs to allow subsequent presentation in the context of an MHC-II molecule and therefore it is not expedient to incorporate D-amino acids in the epitopes used in the present invention.

One especially preferred PADRE peptide is the one having the amino acid sequence AKFVAAWTLKAAA (SEQ ID NO: 3) or an immunologically effective subsequence thereof. This, and other epitopes having the same lack of MHC restriction are preferred T-cell epitopes that should be present in the modified CEA used in the inventive method. Such super-promiscuous epitopes will allow for the simplest embodiments of the invention wherein only one single modified CEA is presented to the vaccinated animal's immune system.

Apart from the $1^{st}$ and $2^{nd}$ antigenic determinants, the immunogen of the invention may also contain other moieties that provide for desirable features of the immunogen. For instance, the immunogen may further comprise at least one moiety coupled to the polyhydroxypolymer, said at least one moiety being selected from is the group consisting of an immune stimulating moiety, a targeting moiety, or a presentation enhancing moiety—these are also discussed in detail below in connection with adjuvants. If such a moiety is a peptide it may be coupled to the activated polyhydroxypolymer in the same step as the coupling of the $1^{st}$ and $2^{nd}$ antigenic determinants.

Hence, the immunogen of the invention can also include the introduction of a moiety which targets the immunogen to an APC or a B-lymphocyte. For instance, the first moiety can be a specific binding partner for a B-lymphocyte specific surface antigen or for an APC specific surface antigen. Many such specific surface antigens are known in the art. For instance, the moiety can be a carbohydrate for which there is a receptor on the B-lymphocyte or the APC (e.g. mannan or mannose). Alternatively, the second moiety can be a hapten. Also an antibody fragment which specifically recognizes a surface molecule on APCs or lymphocytes can be used as a first moiety (the surface molecule can e.g. be an FCγ receptor of macrophages and monocytes, such as FCγRI or, alternatively any other specific surface marker such as CD40 or CTLA-4). It should be noted that all these exemplary targeting molecules can be used as part of an adjuvant, cf. below. CD40 ligand, antibodies against CD40, or variants thereof which bind CD40 will target the modified CEA to dendritic cells. At the same time, recent results have shown that the interaction with the CD40 molecule renders the $T_H$ cells unessential for obtaining a CTL response. Hence, it is contemplated that the general use of CD40 binding molecules as the first moiety (or as adjuvants, cf. below) will enhance the CTL response considerably; in fact, the use of such CD40 binding molecules as adjuvants and "first moieties" in the meaning of the present invention is believed to be inventive in its own right.

As an alternative or supplement to targeting the immunogen to a certain cell type in order to achieve an enhanced immune response, it is possible to increase the level of responsiveness of the immune system by including the an immune system stimulating moiety. Typical examples of such moieties are cytokines, heat-shock proteins, and hormones, as well as effective parts thereof.

Suitable cytokines to be used according to the invention are those which will normally also function as adjuvants in a vaccine composition, e.g. interferon γ (IFN-γ), Flt3 ligand (Flt3L), interleukin 1 (IL-1), interleukin 2 (IL-2), interleukin 4 (IL-4), interleukin 6 (IL-6), interleukin 12 (IL-12), interleukin 13 (IL-13), interleukin 15 (IL-15), and granulocyte-macrophage colony stimulating factor (GM-CSF); alternatively, the functional part of the cytokine molecule may suffice as the second moiety. With respect to the use of such cytokines as adjuvant substances, cf. the discussion below.

Alternatively, the immune stimulating moiety can be a toxin, such as listeriolycin (LLO), lipid A and heat-labile enterotoxin. Also, a number of mycobacterial derivatives such as MDP (muramyl dipeptide), CFA (complete Freund's adjuvant) and the trehalose diesters TDM and TDE are interesting possibilities.

According to the invention, suitable heat shock proteins used as the immune stimulating moiety can be HSP70, HSP90, HSC70 (a heat shock cognate), GRP94, and calreticulin (CRT). Finally, CpG motifs and the immune stimulating peptide tuftsin are other possibilities.

Also the possibility of introducing a presentation enhancing moiety is an important embodiment of the invention. The art has shown several examples of this principle. For instance, it is known that the palmitoyl lipidation anchor in the Borrelia burgdorferi protein OspA can be utilised so as to provide self-adjuvating polypeptides (cf. e.g. WO 96/40718). It seems that the lipidated proteins form up micelle-like structures with a core consisting of the lipidation anchor parts of the polypeptides and the remaining parts of the molecule protruding therefrom, resulting in multiple presentations of the antigenic determinants. Hence, the use of this and related approaches using different lipidation anchors (e.g. a myristyl group, a farnesyl group, a geranyl-geranyl group, a GPI-nchor, and an N-acyl diglyceride group) are preferred embodiments of the invention, especially since the provision of such a lipidation anchor in a recombinantly produced protein is fairly straightforward and merely requires use of e.g. a naturally occurring signal sequence as a fusion partner for a component of the immunogen. Another possibility is use of the C3d fragment of complement factor C3 or C3 itself (cf. Dempsey et al., 1996, Science 271, 348–350 and Lou & Kohler, 1998, Nature Biotechnology 16, 458–462).

The Polyhydroxypolymer Carrier

In order for amino acid sequences to couple to the polyhydroxypolymer it is normally necessary to "activate" the polyhydroxypolymer with a suitable reactive group that can form the necessary link to the amino acid sequences.

The term "polyhydroxypolymer" is generally intended to have the same meaning as in WO 00/05316, i.e. the polyhydroxypolymer can have exactly the same characteristics as is specifically taught in that application. Hence, the polyhydroxypolymer can be water soluble or insoluble (thus requiring different synthesis steps during preparation of the immunogen). Both embodiments given rise to certain advantages. In general, the coupling of peptides to a water-soluble activated polyhydroxypolymer is chemically simpler than the synthesis applicable for an insoluble polymer. It is also contemplated that induction of CTLs will be facilitated by using water-soluble carriers in the invention since such immunogens would be likely to be taken up via pinocytosis. On the other hand, the insoluble polymer can, when grinded, form a particulate composition that is believed to be well-suited for inducing T-cell help due to it being predominantly taken up by APCs and since it results in local concentration of antigen. It is therefore also within the scope of the present invention to utilise vaccination strategies where both water-soluble and water-insoluble immunogens are utilised.

In the event the polymer is dextran, water soluble forms are in general linear molecules, whereas the water insoluble forms of dextran are cross-linked.

The polyhydroxypolymer can be selected from naturally occurring polyhydroxy compounds and synthetic polyhydroxy compounds.

Specific and preferred polyhydroxypolymers are polysaccharides selected from acetan, amylopectin, gum agar-agar, agarose, alginates, gum Arabic, carregeenan, cellulose, cyclodextrins, dextran, furcellaran, galactomannan, gelatin, ghatti, glucan, glycogen, guar, karaya, konjac/A, locust bean gum, mannan, pectin, psyllium, pullulan, starch, tamarine, tragacanth, xanthan, xylan, and xyloglucan. Dextran is especially preferred.

However, the polyhydroxypolymer can also be selected from highly branched poly(ethyleneimine)(PEI), tetrathienylene vinylene, Kevlar (long chains of poly-paraphenyl terephtalamide), Poly(urethanes), Poly(siloxanes), polydimethylsiloxane, silicone, Poly(methyl methacrylate) (PMMA), Poly(vinyl alcohol), Poly(vinyl pyrrolidone), Poly(2-hydroxymethylmethacrylate), Poly(N-vinyl pyrrolidone), Poly(vinyl alcohol), Poly(acrylic acid), Polytetrafluoroethylene (PTFE), Polyacrylamide, Poly(ethylene-covinyl acetate), Poly(ethylene glycol) and derivatives, Poly(methacrylic acid), Polylactides (PLA), Polyglycolides (PGA), Poly(lactide-co-glycolides) (PLGA), polyvinylalcohol, poly(hydroxymethylmethacrylate), poly(hydroxyethylmethacrylate), poly(hydroxypropylmethacrylate)Polyanhydrides, and Polyorthoesters, as well as corresponding copolymers.

The (weight) average molecular weight of the polyhydroxypolymer in question (i.e. before activation) is at least 500, typically at least 1,000, such as at least 2,000, preferably in the range of 2,500–2,000,000, more preferably in the range of 3,000–1,000,000, in particular in the range of 5,000–500,000. It is believed that polyhydroxypolymers having an average molecular weight in the range of 10,000–200,000 are particularly advantageous.

When using a water-soluble polyhydroxypolymer, it is preferably water soluble to an extent of at least 10 mg/ml, preferably at least 25 mg/ml, such as at least 50 mg/ml, in particular at least 100 mg/ml, such as at least 150 mg/ml at room temperature. It is known that dextran, even when activated as described herein, fulfils the requirements with respect to water solubility.

For some of the most interesting polyhydroxypolymers, the ratio between C (carbon atoms) and OH groups (hydroxy groups) of the unactivated polyhydroxypolymers (i.e. the native polyhydroxypolymer before activation) is in the range of 1.3 to 2.5, such as 1.5–2.3, preferably 1.6–2.1, in particular 1.85–2.05. Without being bound to any specific theory, it is believed that such as a C/OH ratio of the unactivated polyhydroxypolymer represents a highly advantageous level of hydrophilicity. Polyvinylalcohol and polysaccharides are examples of polyhydroxypolymers which fulfil this requirement. It is believed that the above-mentioned ratio should be roughly the same for the activated polyhydroxypolymer as the activation ratio should be rather low.

As mentioned above, the polyhydroxypolymers carry functional groups (activation groups), which facilitates the anchoring of peptides to the carrier. A wide range of applicable functional groups are known in the art, e.g. tresyl (trifluoroethylsulphonyl), maleimido, p-nitrophenyl cloroformate, cyanogenbromide, tosyl (p-toluenesulfonyl), triflyl (trifluoromethanesulfonyl), pentafluorobenzenesulfonyl, and vinyl sulphone groups. Preferred examples of functional groups within the present invention are tresyl, maleimido, tosyl, triflyl, pentafluorobenzenesulfonyl, p-nitrophenyl cloroformate, and vinylsulphone groups, among which tresyl, maleimido, and tosyl groups are particularly relevant.

Tresyl activated polyhydroxypolymers can be prepared using tresyl chloride as described for activation of dextran in Example 1 in WO 00/05316 or as described in Gregorius et al., J. Immunol. Meth. 181 (1995) 65–73.

Maleimido activated polyhydroxypolymers can be prepared using p-maleimidophenyl isocyanate as described for activation of dextran in Example 3 of WO 00/05316. Alternatively, maleimido groups could be introduced to a polyhydroxypolymer, such as dextran, by derivatisation of a tresyl activated polyhydroxypolymer (such as tresyl activated dextran (TAD)) with a diamine compound (generally $H_2N-C_nH_{2n}-NH_2$, where n is 1–20, preferably 1–8), e.g. 1,3-diaminopropane, in excess and subsequently react the amino groups introduced in TAD with reagents such as succinimidyl 4-N-aleimidomethyl)cyclohexane-1-carboxylate (SMCC), sulfouccinimidyl 4-(N-maleimidomethyl)cyclohexane-l-carboxylate (sulfo-SMCC), succinimidyl 4-(p-maleimidophenyl)butyrate (SMPB), sulfo-uccinimidyl 4-(p-maleimidophenyl)butyrate (sulfo-MPB), N-γ-maleimidobutyryloxy-succinimide ester (GMBS) or N-γ-maleimidobutyryloxy-sulfosuccinimide ester. Although the different reagents and routes for activation formally results in slightly different maleimide activated products with respect to the linkage between the maleimide functionality and the remainder of the parent hydroxy group on which activation is performed, all and every are considered as "maleimide activated polyhydroxypolymers".

Tosyl activated polyhydroxypolymers can be prepared using tosyl chloride as described for activation of dextran in Example 2 in WO 00/05316. Triflyl and pentafluorobenzenesulfonyl activated polyhydroxypolymers are prepared as the tosyl or tresyl activated analogues, e.g. by using the corresponding acid chlorides.

Cyanogenbromide activated polyhydroxypolymer can be prepared by reacting the polyhydroxypolymer with cyanogenbromide using conventional methods. The resulting functional groups are normally cyanate esters with two hydroxy groups of the polyhydroxypolymer.

The degree of activation can be expressed as the ratio between the free hydroxy groups and the activation groups (i.e. functionalised hydroxy groups). It is believed that a ratio between the free hydroxy groups of the polyhydroxypolymer and the activation groups should be between 250:1 and 4:1 in order to obtain an advantageous balance between the hydrophilicity and the reactivity of the polyhydroxypolymer. Preferably the ratio is between 100:1 and 6:1, more preferably between 60:1 and 8:1, in particular between 40:1 and 10:1.

Especially interesting activated polyhydroxypolymers for use in the method for producing the generally applicable immunogen according to the invention are tresyl, tosyl and maleimido activated polysaccharides, especially tresyl activated dextran (TAD), tosyl activated dextran (TosAD), and maleimido activated dextran (MAD).

The polyhydroxypolymer carrier may be substantially free of amino acid residues, necessitating that the activation group provides for part of a peptidase cleavable bond since the antigenic determinant would not otherwise be able to enter the antigen processing steps of the APC's metabolism.

However, as mentioned, the carrier may also simply include a spacer including at least one L-amino acid. Nevertheless, the at least first and at least second antigenic determinants are normally bound to the activated version of the polyhydroxypolymer via a nitrogen, preferably at the N-terminus of an amino acid sequence.

In brief, in the preferred embodiments of the invention where either of the antigenic determinants may be a peptide, the activated polyhydroxypolymer must normally contain at least one amino acid group if the bond between an amino acid and the activation group cannot be broken by the APC's biochemical machinery. The at least one amino acid group(s) then serves as spacer(s) between the activation group and the antigenic peptide determinant, with the consequence that the bond between the carrier's amino acid(s) and the peptide determinant may be cleaved, leaving the peptide free for attack by peptidases of the APC's processing pathway. Of course, the binding between an activation group and a peptide determinant need not be sensitive to peptidase cleavage—it may equally well be sensitive to other physicochemical conditions that are found in the APC. The important goal to achieve is that the antigenic determinant is liberated inside the APC, thus allowing for binding to an MHC molecule and subsequent presentation to lymphocytes.

Preparation of Immunogen of the Invention

When using the preferred peptide determinants, it is possible to synthesise the peptides so as to protect all available amino groups but the one at the N-terminus, subsequently couple the resulting protected peptides to the activated polyhydroxypolymer moiety, and finally de-protecting the resulting conjugate. A specific example of this approach is described in the examples below—it will, however, be appreciated by the skilled person in peptide chemistry, that multiple methods for obtaining this effect may be employed.

Instead of using the water-soluble polysaccharide molecules as taught in WO 00/05316 and U.S. Pat. No. 5,874,469, it is, as mentioned above, equally possible to utilise cross-linked polysaccharide molecules, thereby obtaining a particulate conjugate between polypeptides and polysaccharide—this is believed to lead to an improved presentation to the immune system of the polypeptides, since two goals are reached, namely to obtain a local deposit effect when injecting the conjugate and to obtain particles which are attractive targets for uptake by APCs. The approach of using such particulate systems is also detailed in the examples, but in general the activated polyhydroxy polymer is used to combine the antigenic determinants containing the B-cell epitope and the T-helper epitopes it can, as mentioned above be performed as a solid phase synthesis and the final product can be harvested and purified by wash and filtration. The elements to be coupled to an activated polyhydroxypolymer (peptides, tags etc) can be added to the polyhydroxypolymer at low pH, e.g. pH 4–5, and allowed to be equally distributed in the "gel" by passive diffusion. Subsequently, the pH can be raised to pH 9–10 to start the reaction of the primary amino groups on the peptides and tags to the tresyl groups on the polyhydroxy polymer. After coupling of peptides and e.g. immune stimulating elements or targeting moieties the gel is grinded to form particles of suitable size for immunization.

The ratio of B-cell epitopes and T-helper epitopes (P2, P30, PADRE or other suitable epitopes) in the final product can be varied by varying the concentration of these molecules in the synthesis step. As mentioned above, the immunogenic molecule can be tagged with e.g. mannose, tuftsin, CpG-motifs or other immune stimulating substances (described herein) by adding these, if necessary by using e.g. aminated derivatives of the substances, to the carbonate buffer in the synthesis step.

Vaccine and Other Immunizing Formulations

When administration of the immunogens of the invention to an animal such as a human being, the formulation of the immunogen follows the principles generally acknowledged in the art. In the following is given a detailed description relevant for peptide vaccines and immunizing compositions since peptides constitute the most preferred embodiments of the above-mentioned $1^{st}$ and $2^{nd}$ antigenic determinants. The skilled reader will, though, appreciate that the general principles given below also will be applicable for most, if not all, vaccine strategies that include an immunogen of the invention.

Preparation of vaccines and immunizing agents that contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables either as liquid solutions or suspensions; solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like, and combinations thereof. In addition, if desired, the vaccine may contain minor amounts of auxiliary substances such as wetting or emulsifying agents, pH buffering agents, or adjuvants which enhance the effectiveness of the vaccines; cf. the detailed discussion of adjuvants below.

The vaccines are conventionally administered parenterally, by injection, for example, either subcutaneously, intracutaneously, or intramuscularly. Additional formulations which are suitable for other modes of administration include suppositories and, in some cases, oral, buccal, sublinqual, intraperitoneal, intravaginal, anal, epidural, spinal, and intracranial formulations. For suppositories, traditional binders and carriers may include, for example, polyalkalene glycols or triglycerides; such suppositories may be formed from mixtures containing the active ingredient in the range of 0.5% to 10%, preferably 1–2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10–95% of active ingredient, preferably 25–70%. For oral formulations, cholera toxin is an interesting formulation partner (and also a possible conjugation partner).

The immunogens may be formulated into the vaccine as neutral or salt forms. Pharmaceutically acceptable salts include acid addition salts (e.g. formed with the free amino groups of a peptide constituting part of an immunogen of the invention) and which are formed with inorganic acids such as, for example, hydrochloric or phosphoric acids, or such organic acids as acetic, oxalic, tartaric, mandelic, and the like. Salts formed with free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms active ingredient per vaccination with a preferred range from about 0.1 µg to 2,000 µg (even though higher amounts in the 1–10 mg range are contemplated), such as in the range from about 0.5 µg to 1,000 µg, preferably in the range from 1 µg to 500 µg and especially in the range from about 10 µg to 100 µg. Suitable regimens for initial administration and booster shots are also variable but are typified by an initial administration followed by subsequent inoculations or other administrations.

The manner of application may be varied widely. Any of the conventional methods for administration of a vaccine are applicable. These include oral application on a solid physiologically acceptable base or in a physiologically acceptable dispersion, parenterally, by injection or the like. The dosage of the vaccine will depend on the route of administration and will vary according to the age of the person to be vaccinated and the formulation of the antigen.

Some of the immunogens of the vaccine are sufficiently immunogenic in a vaccine, but for some of the others the immune response will be enhanced if the vaccine further comprises an adjuvant substance.

Various methods of achieving adjuvant effect for the vaccine are known. General principles and methods are detailed in "The Theory and Practical Application of Adjuvants", 1995, Duncan E. S. Stewart-Tull (ed.), John Wiley & Sons Ltd, ISBN 0-471-95170-6, and also in "Vaccines: New Generation Immunological Adjuvants", 1995, Gregoriadis G et al. (eds.), Plenum Press, New York, ISBN 0-306-45283-9, both of which are hereby incorporated by reference herein.

It is especially preferred to use an adjuvant which can be demonstrated to facilitate breaking of the autotolerance to self-protiens and other haptens that are not merely non-immunogenic due to their small size; however, in cases where the antigenic determinants coupled to the polyhydroxy polymer are both sufficiently large and sufficiently immunogenic, the adjuvant need not be incorporated.

Non-limiting examples of suitable adjuvants are selected from the group consisting of an immune targeting adjuvant; an immune modulating adjuvant such as a toxin, a cytokine, and a mycobacterial derivative; an oil formulation; a polymer; a micelle forming adjuvant; a saponin; an immunostimulating complex matrix (ISCOM matrix); a particle; DDA; aluminium adjuvants; DNA adjuvants; γ-inulin; and an encapsulating adjuvant. In general it should be noted that the disclosures above which relate to compounds and agents useful as moieties in the immunogens also refer mutatis mutandis to their use in the adjuvant of a vaccine of the invention—in other words, instead of being part of the immunogen of the invention, such moieties are also suited as parts of the formulations of the present invention.

The application of adjuvants include use of agents such as aluminium hydroxide or phosphate (alum), commonly used as 0.05 to 0.1 percent solution in buffered saline, admixture with synthetic polymers of sugars (e.g. Carbopol®) used as 0.25 percent solution, aggregation of protein in the vaccine by heat treatment with temperatures ranging between 70° to 101° C. for 30 second to 2 minute periods respectively and also aggregation by means of cross-linking agents are possible. Aggregation by reactivation with pepsin treated antibodies (Fab fragments) to albumin, mixture with bacterial cells such as *C. parvum* or endotoxins or lipopolysaccharide components of gram-negative bacteria, emulsion in physiologically acceptable oil vehicles such as mannide monooleate (Aracel A) or emulsion with 20 percent solution of a perfluorocarbon (Fluosol-DA) used as a block substitute may also be employed. Admixture with oils such as squalene and IFA is also preferred.

According to the invention DDA (dimethyldioctadecylammonium bromide) is an interesting candidate for an adjuvant as is DNA and γ-inulin, but also Freund's complete and incomplete adjuvants as well as quillaja saponins such as QuilA and QS21 are interesting as is RIBI. Further possibilities are monophosphoryl lipid A (MPL), the above mentioned C3 and C3d, and muramyl dipeptide (MDP).

Liposome formulations are also known to confer adjuvant effects, and therefore liposome adjuvants are preferred according to the invention.

Also immunostimulating complex matrix type (ISCOM® matrix) adjuvants are preferred choices according to the invention, especially since it has been shown that this type of adjuvants are capable of up-regulating MHC Class II expression by APCs. An ISCOM® matrix consists of (optionally fractionated) saponins (triterpenoids) from *Quillaja saponaria*, cholesterol, and phospholipid. When admixed with the immunogenic protein, the resulting particulate formulation is what is known as an ISCOM particle where the saponin constitutes 60–70% w/w, the cholesterol and phospholipid 10–15% w/w, and the protein 10–15% w/w. Details relating to composition and use of immunostimulating complexes can e.g. be found in the above-mentioned text-books dealing with adjuvants, but also Morein B et al., 1995, Clin. Immunother. 3: 461–475 as well as Barr I G and Mitchell G F, 1996, Immunol. and Cell Biol. 74: 8–25 (both incorporated by reference herein) provide useful instructions for the preparation of complete immunostimulating complexes.

Another highly interesting (and thus, preferred) possibility of achieving adjuvant effect is to employ the technique described in Gosselin et al., 1992 (which is hereby incorporated by reference herein). In brief, the presentation of a relevant antigen such as an antigen of the present invention can be enhanced by conjugating the antigen to antibodies (or antigen binding antibody fragments) against the Fcγ receptors on monocytes/macrophages. Especially conjugates between antigen and anti-FcγRI have been demonstrated to enhance immunogenicity for the purposes of vaccination.

Other possibilities involve the use of the targeting and immune modulating substances (i.a. cytokines) mentioned in the claims as moieties for the protein constructs. In this connection, also synthetic inducers of cytokines like poly I:C are possibilities.

Suitable mycobacterial derivatives are selected from the group consisting of muramyl dipeptide, complete Freund's adjuvant, RIBI, and a diester of trehalose such as TDM and TDE.

Suitable immune targeting adjuvants are selected from the group consisting of CD40 ligand and CD40 antibodies or specifically binding fragments thereof (cf. the discussion above), mannose, a Fab fragment, and CTLA-4.

Suitable polymer adjuvants are selected from the group consisting of a carbohydrate such as dextran, PEG, starch, mannan, and mannose; a plastic polymer; and latex such as latex beads.

Yet another interesting way of modulating an immune response is to include the immunogen (optionally together with adjuvants and pharmaceutically acceptable carriers and vehicles) in a "virtual lymph node" (VLN) (a proprietary medical device developed by ImmunoTherapy, Inc., 360 Lexington Avenue, New York, N.Y. 10017-6501). The VLN (a thin tubular device) mimics the structure and function of a lymph node. Insertion of a VLN under the skin creates a site of sterile inflammation with an upsurge of cytokines and chemokines. T- and B-cells as well as APCs rapidly respond to the danger signals, home to the inflamed site and accumulate inside the porous matrix of the VLN. It has been shown that the necessary antigen dose required to mount an immune response to an antigen is reduced when using the VLN and that immune protection conferred by vaccination using a VLN surpassed conventional immunization using Ribi as an adjuvant. The technology is i.a. described briefly in Gelber C et al., 1998, "Elicitation of Robust Cellular and Humoral Immune Responses to Small Amounts of Immunogens Using a Novel Medical Device Designated the Virtual Lymph Node", in: "From the Laboratory to the Clinic, Book of Abstracts, Oct. $12^{th}$–$15^{th}$ 1998, Seascape Resort, Aptos, Calif.".

It is expected that the vaccine of the invention should be administered at least once a year, such as at least 1, 2, 3, 4, 5, 6, and 12 times a year. More specifically, 1–12 times per year is expected, such as 1, 2, 3, 4, 5, 6, 7, 8, 9, 10, 11, or 12 times a year to an individual in need thereof. It has previously been shown that the memory immunity induced by the use of the preferred autovaccines according to the invention is not permanent, and therefor the immune system needs to be periodically challenged with the analogues.

Due to genetic variation, different individuals may react with immune responses of varying strength to the same polypeptide. Therefore, the vaccine according to the invention may comprise several different immunogens with differences in the choice of antigenic determinants in order to increase the immune response, cf. also the discussion above concerning the choice of foreign T-cell epitope introductions. The vaccine may comprise two or more immunogens, where all of the immunogens are as defined above.

The vaccine may consequently comprise 3–20 different immunogens of the invention, such as 3–10 immunogens. However, normally the number of analogues will be sought kept to a minimum such as 1 or 2 analogues, especially because the immunogens may be tailored to include both the necessary $1^{st}$ antigenic determinants and the necessary $2^{nd}$ antigenic determinants in order to target as large a fraction of the vaccinated population.

Identifying Useful Immunogens

As mentioned above, an advantage of the immunogens of the invention is that they can be tailored to provide the optimum ratio between $1^{st}$ and $2^{nd}$ antigenic determinants. This also allows for the provision of a method for selection and preparation of useful immunogens of the invention. The method entails preparation of at least two different immunogens of the invention where each different immunogen has a characteristic ratio between the $1^{st}$ and $2^{nd}$ antigenic determinants. These immunogens are then formulated as immunizing agents (cf. example 3) and their respective capabilities of inducing a specific immune response against the $1^{st}$ antigenic determinant are determined. The most effective immunogen(s) is/are selected and used for further development.

A similar approach can be used when determining the precise relative amount of targeting or immunostimulating moieties that should be incorporated in the immunogens of the invention in order to obtain the best efficacy.

The $1^{st}$ and $2^{nd}$ antigenic determinants as well as possible further moieties are coupled to the activated polyhydroxypolymer essentially as described in the present examples. And since the ratio of incorporated molecules in the immunogen is dependent on the relative concentrations of the molecules in the incubation mixture, it is unproblematic to prepare a large number of different immunogens merely be adjusting the relative concentrations of the molecules.

The present invention will now be illustrated by means of the following non-limiting examples.

EXAMPLE 1

Synthesis of an Aβ Peptide Copolymer Vaccine using Activated Poly-Hydroxypolymer as the Cross-Linking Agent.

Introduction.

A traditional conjugate vaccine consists of an antigen or hapten (e.g. in the form of a polypeptide antigen or hapten) coupled covalently to a carrier, such as a carrier protein. The antigen/hapten contains the B-cell or CTL epitope(s) and the carrier protein provides $T_H$ epitopes. However, most of the carrier protein will normally be irrelevant as a source for $T_H$ epitopes, since only a minor part of the total sequence contains the relevant $T_H$ epitopes. Such epitopes can be defined and synthesized as peptides of e.g. 9–15 amino acids. If these peptides are linked covalently to peptides containing the B-cell or CTL epitopes, e.g. via a multivalent activated polyhydroxypolymer as taught herein, a vaccine molecule that only contains the relevant parts of the antigen and the traditional carrier can be obtained. It is further possible to provide an immunogen that contains an optimized composition of B-cell epitopes, CTL epitopes, and $T_H$ epitopes.

Synthesis of the Activated Poly-Hydroxypolymer.

Polyhydroxypolymers such as dextran, starch, agarose etc. can be activated with 2,2,2-trifluoroethanesulfonyl chloride (tresyl chloride), either by means of a homogenous synthesis (dextran) dissolved in N-methylpyrrolidinone (NMP) or by means of a heterogeneous synthesis (starch, agarose, cross-linked dextran) in e.g. acetone.

225 ml dry N-methyl pyrrolidinone (NMP) is added under dry conditions to freeze dried, water-soluble dextran (4.5 g, 83 mmol, clinical grade, Mw(avg) 78000) in a 500 ml round bottom flask supplied with a magnet for stirring. The flask is placed in a 60° C. oil bath with magnetic stirring. The temperature is raised to 92° C. over a period of 20 min. When the dextran is dissolved the flask is immediately removed from the oil bath and the temperature in the bath is lowered to 40° C. The flask is placed into the oil bath agaom, still with magnetic stirring, and tresyl chloride (2.764 ml, 25 mmol) is added drop-wise. After 15 min, dry pyridine (anhydrous, 2.020 ml, 25 mmol) is added drop-wise. The flask is removed from the oil bath and stirred for 1 hour at room temperature. The product (Tresyl Activated Dextran, TAD) is precipitated in 1200 ml cold ethanol (99.9%). The supernatant is decanted and the precipitate is harvested in 50 ml polypropylene tubes in a centrifuge at 2000 rpm. The precipitate is dissolved in 50 ml 0.5% acetic acid, dialyzed 2 times against 5000 ml 0.5% acetic acid and freeze-dried. TAD can be stored as a freeze-dried powder at −20° C.

Alternatively, an insoluble poly-hydroxypolymer, such as agarose or cross-linked dextran can be tresyl activated by making a suspension of the poly-hydroxypolymer in e.g. acetone and perform the synthesis as a solid phase synthesis. The activated polyhydroxypolymer can be harvested by filtration. Suitable methods are reported in e.g. Nilsson K and Mosbach K (1987), Methods in Enzymology 135, p. 67, and in Hermansson G T et al. (1992), in "Immobilized Affinity Ligand Techniques", Academic Press, Inc., p. 87.

Synthesis of the Immunogens of the Invention—Human Aβ-42 as an Exemplary Peptide Antigen.

TAD (10 mg) is dissolved in 100 μl H$_2$O and 1000 μl carbonate buffer, pH 9.6, containing 5 mg Aβ-42 (SEQ ID NO: 2, residues 673–714), 2.5 mg P2 (SEQ ID NO: 1) and 2.5 mg P30 (SEQ ID NO: 2) is added. The Aβ-42 and the P2 and P30 peptides all contain protected lysine groups: these are in the form of 1-(4,4-Dimethyl-2,6-dioxocyclohex-1-ylidene)ethyl (Dde) protected lysine groups. The peptides are prepared by means of a standard Fmoc strategy, where the con-ventional Fmoc-Lys(Boc)-OH has been substituted with Fmoc-Lys(Dde)-OH (obtained from Novabiochem, cat. no. 04-12-1121), i.e. the ε-amino group in lysine is protected with Dde instead of Boc.

The pH value is measured and adjusted to 9.6 using 1 M HCl. After 2.5 hours at room temperature, hydrazine from an 80% so-lution is added to a final hydrazine concentration of 8% and the solution is incubated for another 30 min. at room temperature and freeze-dried immediately thereafter. The freeze-dried product is dissolved in H$_2$O and dialysed extensively against H$_2$O before the final freeze-drying.

The ratio between B-cell epitopes (Aβ) and T-helper epitopes (P2 and P30) in the final product is varied using different concentrations of these peptides in the synthesis step. Furthermore, the final product can be tagged with e.g. mannose (so as to target the conjugate to APCs) by adding aminated mannose to the carbonate buffer in the synthesis step.

If an insoluble activated poly-hydroxypolymer is used to combine the peptides containing the B-cell epitope and the T-helper epitopes, the coupling to the polymer can be performed as a traditional solid phase synthesis and the final product is harvested and purified by wash and filtration.

As mentioned in the general description, the presently described approach for preparing a peptide based vaccine may be applied to any other polypeptide antigen where it would be convenient to prepare a purely synthetic peptide vaccine and where the polypeptide antigen in question provides sufficient immunogenicity in one single peptide:

EXAMPLE 2

General Synthesis Peptide Copolymer Vaccines

TAD (10 mg) is dissolved in 100 μl H$_2$O and 1000 μl carbonate buffer, pH 9.6, containing 1–5 mg peptide A (any immunogenic peptide of interest), 1–5 mg P2 (diphtheria toxoid P2 epitope) and 1–5 mg P30 (diphtheria toxoid P30 epitope) is added. The pH value is measured and adjusted to 9.6 using 0.1 M HCl. After 2.5 hours at room temperature the solution is freeze dried immediately hereafter. The freeze-dried product is dissolved in H$_2$O and dialysed extensively against H$_2$O or desalted on a gelfiltration column before the final freeze-drying. In case the peptides have lysine in the sequence the ε-amine in the lysine side chain should be protected by Dde using the Fmoc-Lys(Dde)-OH derivative in the synthesis (Gregorius and Theisen 2001, submitted). After coupling, hydrazine from an 80% solution is added to a final hydrazine concentration between 1–20% and the solution is incubated for another 30 min at room temperature, freeze dried immediately hereafter and dialysed extensively against H$_2$O or desalted on a gelfiltration column before the final freeze-drying. The principle is set forth in schematic form in FIG. 2.

Such immunogens have been utilised by the inventors with the short 8 amino acid C-terminal fragment of the *Borrelia burgdorferi* protein OspC as "peptide A" and a diptheria toxoid epitope (P2 or P30) as peptide B. The results of immunization studies with this antigen revealed that only the immunogen of the invention including the OspC fragment and a foreign diptheria epitope matching the MHC haplotype of the vaccinated mice were capable of inducing antibodies reactive with OspC in these mice. In contrast, a molecule containing only the OspC peptide was unable to induce antibody production and the same was true for a mixture of 2 immunogens where one contained the OspC and the other the epitope. It is therefore concluded that the inclusion in the same polyhydroxypolymer carrier is superior, if not essential, in order to induce antibody production against a short peptide hapten as OspC.

The above referenced experiment with the C-terminal OspC fragment has also demonstrated that coupling of peptides to TAD provides for an immunogen that is capable of triggering T$_H$ lymphocytes that provide specific T-cell help. This means that the immunogen is 1) capable of being taken up by APCs and 2) that the APCs are subsequently capable of processing the immunogen so as to present the T$_H$ epitopes in an MHC Class II context to T$_H$ lymphocytes. To the best of the present inventors' beliefs, the capacity of a polyhydroxypolymer to accomplish this effect has never been demonstrated previously.

EXAMPLE 3

Vaccination and Efficacy Determination

Vaccinations

The immunogen of the invention is injected into a suitable animal species such as mouse, rat, guinea pig, rabbit, or monkey.

The immunogens can be mixed with a suitable adjuvant such as for example Freund's Adjuvant, ISA-51, aluminum-based adjuvants (aluminium phosphate or aluminium hydroxide, e.g. from Danfoss), Calcium Phosphate, QS21 (Antigenics), MF59 (Chiron Corp.), and Ribi (Glaxo Smith-Kline). Protein vaccines are usually administered 3–5 times, for example at weeks 0, 3, 6, 9, 12.

Antibody Titer Determination

Sera from vaccinated animals can be tested for specific antibodies by ELISA. 96-well Maxisorb plates (e.g obtained from Nunc, Life Technologies, Taastrup, Denmark) can be coated with a suitable volume (e.g. 50 ul) of either the antigen from which the 1$^{st}$ antigenic determinant is derived or with the antigenic determinant as such. This is done in a suitable buffer such as carbonate buffer pH 9.6 in a suitable concentration giving a final content of e.g. 1 ug/well. The plates are incubated, e.g. for 1 hour, washed in washing buffer, e.g. PBS+0.5M NaCl+1% Triton X-100 and then blocked for e.g. 1 hour in dilution buffer that could e.g. be washing buffer plus 1% BSA. Standards and diluted serum samples can be added in duplicate and incubated in the plates, e.g. for 30 minutes. After washing, a dilution of secondary antibody (e.g. HRP conjugated rabbit-anti-mouse IgG e.g. from DAKO, Glostrup, Denmark) can be added (e.g diluted 1:1000 in dilution buffer) and incubated for 30 minutes. The plates can then be washed in washing buffer, and a chromogenic substrate, e.g. OPD substrate (e.g. from Sigma-Aldrich, Vallensbak Strand, Denmark) can be added.

The reaction can be stopped with e.g 2N H$_2$SO$_4$ and the optical density be measured in e.g. a Dynex MRX ELISA plate reader at 490 nm. Serum antibody concentrations can be calculated e.g. by relating the optical densities of the samples to a standard curve. In general, there are many antibodies available from commercial or academic sources—these antibodies can be used to generate a standard curve, but in the event such an antibody should not be available, it can be prepared by methods known in the art.

The ELISA can be modified for different purposes. Sandwich ELISA can be used to monitor whether the antisera contains reactivities that can displace e.g. a biotin-labeled, therapeutically relevant antibody from binding to plate-coated antigen or 1$^{st}$ antigenic determinant. Specialized ELISA kits can be used to determine the isotype subclass distribution in antisera etc.

Assays to Monitor Anti-CEA CTL Activity

It can be investigated whether immunization with CTL epitope containing vaccines can induce an antigen-specific CTL response. The CTL epitopes used in the immunogen can be used to pulse APCs in e.g. typical cytotoxic T cell assays. Antigen-expressing target cells (e.g. MHC class I expressing cell lines transfected with a gene encoding the antigen of interest) can be used as targets for antigen-specific cytotoxic T lymphocytes (CTLs). Mice will be vaccinated with the inventive immunogens using an appropriate vaccination scheme, cf. above. As positive control, mice could be immunized with e.g. MHC class I peptides derived from the antigen sequence. After a suitable time interval, e.g. three weeks after the first immunization, splenocytes from immunized mice can be re-stimulated e.g. with mytomicin C-treated (e.g. 50 µg/ml, 20 min at 37° C.) syngeneic splenocytes loaded with the peptides. For this re-stimulation process, a suitable number (e.g. 100×10$^6$) of peptide-loaded syngeneic splenocytes can be mixed with a suitable number (e.g. 60×10$^6$) of splenocytes from vaccinated mice in and incubated at 37° C. for e.g. 7 days. After the restimulation process, the cytotoxic activity of the effector cells can be monitored e.g. in a chromium release assay. A suitable number (e.g. 5×10$^6$) of target cells is labeled with $^{51}$Chromium (e.g. 200 mCi), if necessary loaded with antigen-derived peptide, and used as targets in a $^{51}$Chromium release assay. Cell lines transfected with the relevant antigen can also be used as targets for CTLs. Such CTL assays can e.g. be performed in normal wild type mice, transgenic mice and/or mice transgenic for human HLA class I molecules (e.g. HHD mice) using suitable compatible target cells and cells for restimulation.

The ability of a vaccine of the invention to induce antigen-specific CTL responses can also be measured using other assay methods including antigen-specific tetramer stainings and Elispot assays; all such methods are well-known to the person skilled in immunology.

The invention will now be further described by the following numbered paragraphs:

1. An immunogen which comprises
   a) at least one first antigenic determinant that includes at least one B-cell epitope and/or at least one CTL epitope, and
   b) at least one second antigenic determinant that includes a T helper cell epitope (T$_H$ epitope),
   wherein each of the at least one first and second antigenic determinants are coupled to a pharmaceutically acceptable activated polyhydroxypolymer carrier.
2. The immunogen according to paragraph 1, wherein the at least one first antigenic determinant is constituted by an amino acid sequence and/or wherein the at least one second antigenic determinant is constituted by an amino acid sequence.
3. The immunogen according to paragraph 1 or 2, wherein the at least first and at least second antigenic determinants are coupled to the polyhydroxypolymer carrier via a bond cleavable by a peptidase.
4. The immunogen according to any one of paragraphs 1–3, wherein the at least first and at least second antigenic determinants are coupled to the activated polyhydroxypolymer carrier via an amide bond or a peptide bond.
5. The immunogen according to paragraph 4, wherein the at least first and at least second antigenic determinants each provide for the nitrogen moiety of their respective bond.
6. The immunogen according to any one of the preceding paragraphs, wherein the polyhydroxypolymer carrier is substantially free of amino acid residues.
7. The immunogen according to paragraph 5 or 6, wherein the at least first and at least second antigenic determinants are bound to the activated polyhydroxypolymer via a nitrogen atom at the N-terminus of an amino acid sequence.
8. The immunogen acccording to any of one of the preceding paragraphs wherein the polyhydroxypolymer is water soluble.
9. The immunogen acccording to any one of paragraphs 1–7 wherein the polyhydroxypolymer is water insoluble.
10. The immunogen according to any one of the preceding paragraphs, wherein the polyhydroxypolymer is selected from naturally occurring polyhydroxy compounds and synthetic polyhydroxy compounds.
11. The immunogen according to any one of the preceding paragraphs, wherein the polyhydroxypolymer is a polysaccharide selected from acetan, amylopectin, gum agar-agar, agarose, alginates, gum Arabic, carregeenan, cellulose, cyclodextrins, dextran, furcellaran, galactomannan, gelatin, ghatti, glucan, glycogen, guar, karaya, konjac/A, locust bean gum, mannan, pectin, psyllium, pullulan, starch, tamarine, tragacanth, xanthan, xylan, and xyloglucan.
12. The immunogen according to paragraph 11, wherein the polyhydroxypolymer is dextran.
13. The immunogen according to any one paragraphs 1–10, wherein the polyhydroxypolymer is selected from highly branched poly(ethyleneimine)(PEI), tetrathienylene vinylene, Kevlar (long chains of poly-paraphenyl terephtalamide), Poly(urethanes), Poly(siloxanes), polydimethylsiloxane, silicone, Poly(methyl methacrylate) (PMMA), Poly(vinyl alcohol), Poly(vinyl pyrrolidone), Poly(2-hydroxy ethyl methacrylate), Poly(N-vinyl pyrrolidone), Poly(vinyl alcohol), Poly(acrylic acid), Polytetrafluoroethylene (PTFE), Polyacrylamide, Poly(ethylene-covinyl acetate), Poly(ethylene glycol) and derivatives, Poly (methacrylic acid), Polylactides (PLA), Polyglycolides (PGA), Poly(lactide-co-glycolides) (PLGA), Polyanhydrides, and Polyorthoesters.
14. The immunogen according to any of the preceding paragraphs, wherein the average molecular weight of the polyhydroxypolymer before activation is at least 500.
15. The immunogen according to any one of the preceding paragraphs, wherein the polyhydroxypolymer is activated with functional groups selected from tresyl (trifluoroethylsulphonyl), maleimido, p-nitrophenyl cloroformate, and tosyl (p-toluenesulfonyl).
16. The immunogen according to any of the preceding paragraphs that further comprises that at least one moiety is coupled to the polyhydroxypolymer, said at least one moiety being selected from the group consisting of an immune stimulating moiety or a targeting moiety.

17. The immunogen according to paragraph 16, wherein the at least one moiety is a peptide.

18. The immunogen according to any of the preceding paragraphs which is capable of being taken up by an antigen presenting cell (APC).

19. The immunogen according to paragraph 18, which is capable of being processed by the APC whereby the APC presents the $T_H$ epitope on its surface bound to an MHC Class II molecule.

20. The immunogen according to any one of the preceding paragraphs wherein the at least one first and second antigenic determinants are not derived from the same naturally occurring molecule.

21. The immunogen according to paragraph 20, wherein the at least one and the at least second antigenic determinants do not occur naturally in the same species.

22. The immunogen according to any one of the preceding paragraphs, wherein the $T_H$ epitope binds strongly to at least one human MHC Class II molecule.

23. The immunogen according to paragraph 22, wherein the $T_H$ epitope is a promiscuous $T_H$ epitope in humans.

24. An immunogenic composition for raising an immune response against an antigen in a mammal, including a human being, comprising the immunogen according to any one of the preceding paragraphs in admixture with a pharmacologically an immunologically acceptable carrier, excipient or diluent, and optionally with an adjuvant.

25. The immunogenic composition according to paragraph 24, wherein the adjuvant is selected from the group consisting of an immune targeting adjuvant; an immune modulating adjuvant such as a toxin, a cytokine and a mycobacterial derivative; an oil formulation; a polymer; a micelle forming adjuvant; a saponin; an immunostimulating complex matrix (an ISCOM matrix); a particle; DDA; aluminium adjuvants; DNA adjuvants; γ-inulin; and an encapsulating adjuvant.

26. A method for immunizing an animal, including a human being, against an antigen of choice, the method comprising administering an effective amount of the immunogen according to any of paragraphs 1–23 or the immunogenic composition according to paragraph 24 or 25 to the animal, wherein the antigen shares the at least one first antigenic determinant with the immunogen.

27. The method according to paragraph 26, wherein the immunogen or the immunogenic composition is administered via a route selected from a route selected from the group consisting of the parenteral route such as the intracutaneous, the subcutaneous, and the intramuscular routes; the peritoneal route; the oral route; the buccal route; the sublingual route; the epidural route; the spinal route; the anal route; and the intracranial route.

28. The method according to paragraph 26 or 27, wherein the effective amount of the immunogen is between 0.5 μg and 2,000 μg.

29. The method according to any of paragraphs 26–28, which includes at least one administration per year, such as at least 2, at least 3, at least 4, at least 6, and at least 12 administrations per year.

30. The method according to any one of paragraphs 26–29, wherein the immunogen or the immunogenic composition is contained in a virtual lymph node (VLN) device.

We claim:

1. An immunogen which comprises
    a) at least one first antigenic determinant constituted by an amino acid sequence that includes at least one B-cell epitope and/or at least one CTL epitope, and
    b) at least one second antigenic determinant constituted by an amino acid sequence that includes a T helper cell epitope (TH epitope), wherein each of the at least one first and second antigenic determinants are independently coupled through the nitrogen atoms at their respective N-termini to a pharmaceutically acceptable activated polyhydroxypolymer carrier via a bond that is cleavable by a peptidase.

2. The immunogen according to claim 1, wherein the at least first and at least second antigenic determinants are coupled to the activated polyhydroxypolymer carrier via an amide bond.

3. The immunogen according to claim 2, wherein the at least first and at least second antigenic determinants each provide for the nitrogen moiety of their respective bond.

4. The immunogen according to claim 2, wherein the amide bond is a peptide bond.

5. The immunogen according to claim 1, wherein the polyhydroxypolymer carrier is substantially free of amino acid residues.

6. The immunogen according to claim 1 wherein the polyhydroxypolymer carrier is water soluble.

7. The immunogen according to claim 1 wherein the polyhydroxypolymer is carrier water insoluble.

8. The immunogen according to claim 1, wherein the polyhydroxypolymer carrier is a naturally occurring polyhydroxy compound.

9. The immunogen according to claim 1, wherein the polyhydroxypolymer carrier is a polysaccharide selected from acetan, amylopectin, gum agar-agar, agarose, alginates, gum Arabic, carregeenan, cellulose, cyclodextrins, dextran, furcellaran, galactomannan, gelatin, ghatti, glucan, glycogen, guar, karaya, konjac/A, locust bean gum, mannan, pectin, psyllium, pullulan, starch, tamarine, tragacanth, xanthan, ,xylan, and xyloglucan.

10. The immunogen according to claim 9, wherein the polyhydroxypolymer carrier is dextran.

11. The immunogen according to claim 1, wherein the polyhydroxypolymer carrier is selected from highly branched poly(ethyleneimine)(PEI), tetrathienylene vinylene, Kevlar (long chains of poly-paraphenyl terephtalamide), Poly(urethanes), Poly(siloxanes), polydimethylsiloxane, silicone, Poly(methyl methacrylate) (PMMA), Poly (vinyl alcohol), Poly(vinyl pyrrolidone), Poly(2-hydroxy ethyl methacrylate), Poly(N-vinyl pyrrolidone), Poly(vinyl alcohol), Poly(acrylic acid), Polytetrafluoroethylene (PTFE), Polyacrylamide, Poly(ethylene-co-vinyl acetate), Poly(ethylene glycol) and derivatives, Poly(methacrylic acid), Polylactides (PLA), Polyglycolides (PGA), Poly(lactide-co-glycolides) (PLGA), Polyanhydrides, and Polyorthoesters.

12. The immunogen according to claim 1, wherein the average molecular weight of the polyhydroxypolymer carrier before activation is at least 500 Daltons.

13. The immunogen according to claim 1 that further comprises that at least one moiety is coupled to the polyhydroxypolymer carrier, said at least one moiety being selected from the group consisting of an immune stimulating moiety or a targeting moiety.

14. The immunogen according to claim 13, wherein the at least one moiety is a peptide.

15. The immunogen according to claim 1 which is capable of being taken up by an antigen presenting cell (APC).

16. The immunogen according to claim 15, which is capable of being processed by the APC whereby the APC presents the TH epitope on its surface bound to an MHC Class II molecule.

17. The immunogen according to claim 1 wherein the at least one first and second antigenic determinants are not derived from the same naturally occurring molecule.

18. The immunogen according to claim 17, wherein the at least one first and second antigenic determinants do not occur naturally in the same species.

19. The immunogen according to claim 1, wherein the TH epitope is a promiscuous TH epitope in humans.

20. An immunogenic composition for raising an immune response against an antigen in a mammal, including a human being, comprising the immunogen according to claim 1 in admixture with a pharmacologically and immunologically acceptable carrier, excipient or diluent, and optionally with an adjuvant.

21. The immunogenic composition according to claim 20, wherein the adjuvant is selected from the group consisting of an immune targeting adjuvant; an immune modulating adjuvant; an oil formulation; a polymer; a micelle forming adjuvant; a saponin; an immunostimulating complex matrix (an ISCOM matrix); an ISCOM particle; DDA; aluminium adjuvants; DNA adjuvants; γ-inulin; and an encapsulating adjuvant.

22. The immunogen according to claim 1, wherein the polyhydroxypolymer carrier is a synthetic polyhydroxy compound.

23. An immunogen which comprises
a) at least one first antigenic determinant constituted by an amino acid sequence that includes at least one B-cell epitope and/or at least one CTL epitope, and
b) at least one second antigenic determinant constituted by an amino acid sequence that includes a T helper cell epitope (TH epitope), wherein each of the at least one first and second antigenic determinants are independently coupled through the nitrogen atoms at their respective N-termini to a pharmaceutically acceptable activated polyhydroxypolymer carrier via a bond that is cleavable by a peptidase, and wherein the polyhydroxypolymer carrier is activated with functional groups selected from tresyl (trifluoroethylsulphonyl), maleimido, p-nitrophenyl cloroformate, and tosyl (p-toluenesulfonyl).

* * * * *